United States Patent [19]

Young

[11] Patent Number: 5,411,944
[45] Date of Patent: May 2, 1995

[54] GLYPHOSATE-SULFURIC ACID ADDUCT HERBICIDES AND USE

[75] Inventor: Donald C. Young, Fullerton, Calif.

[73] Assignee: Union Oil Company of California, Los Angeles, Calif.

[21] Appl. No.: 171,190

[22] Filed: Dec. 21, 1993

Related U.S. Application Data

[60] Continuation of Ser. No. 887,288, May 22, 1992, abandoned, which is a division of Ser. No. 306,529, Feb. 3, 1989, Pat. No. 5,116,401, which is a continuation of Ser. No. 890,076, Jul. 24, 1986, abandoned, which is a continuation-in-part of Ser. No. 771,260, Aug. 30, 1985, abandoned, and a continuation-in-part of Ser. No. 673,358, Nov. 20, 1984, Pat. No. 4,664,717, and a continuation-in-part of Ser. No. 442,296, Nov. 17, 1982, abandoned, and a continuation-in-part of Ser. No. 444,667, Nov. 26, 1982, abandoned, and a continuation-in-part of Ser. No. 453,496, Dec. 27, 1982, Pat. No. 4,910,179, which is a continuation-in-part of Ser. No. 331,001, Dec. 15, 1991, Pat. No. 4,402,852, and a continuation-in-part of Ser. No. 330,904, Dec. 15, 1981, Pat. No. 4,404,116, and a continuation-in-part of Ser. No. 318,629, Nov. 5, 1981, Pat. No. 4,445,925, and a continuation-in-part of Ser. No. 318,368, Nov. 5, 1981, Pat. No. 4,447,253, and a continuation-in-part of Ser. No. 318,343, Nov. 5, 1981, Pat. No. 4,397,675.

[51] Int. Cl.$^6$ ............... A01N 57/04; A01N 59/02
[52] U.S. Cl. ............... 504/206; 504/123
[58] Field of Search ............... 504/206, 123

[56] References Cited

U.S. PATENT DOCUMENTS

| | | | |
|---|---|---|---|
| 3,799,758 | 3/1974 | Franz | 504/206 |
| 4,199,345 | 4/1980 | Franz | 71/86 |
| 4,214,888 | 7/1980 | Young | 71/28 |
| 4,233,056 | 11/1980 | Maier | 71/86 |
| 4,310,343 | 1/1982 | Verdegaal et al. | 71/28 |
| 4,315,763 | 2/1982 | Stoller et al. | 71/29 |
| 4,366,232 | 12/1982 | Buser et al. | 430/390 |
| 4,397,675 | 8/1983 | Young | 71/28 |
| 4,402,852 | 9/1983 | Young | 252/182 |
| 4,404,116 | 9/1983 | Young | 252/182 |
| 4,405,531 | 9/1983 | Franz | 260/501.12 |
| 4,445,925 | 5/1984 | Young | 71/28 |
| 4,447,253 | 5/1984 | Young | 71/28 |
| 4,512,813 | 4/1985 | Young | 134/27 |
| 4,522,644 | 6/1985 | Young | 71/78 |
| 4,589,925 | 5/1986 | Young | 134/3 |
| 4,626,417 | 12/1986 | Young | 423/235 |
| 4,664,717 | 5/1987 | Young | 127/37 |
| 4,673,522 | 6/1987 | Young | 252/87 |
| 4,686,017 | 8/1987 | Young | 204/45.1 |
| 4,722,986 | 2/1988 | Young | 527/203 |
| 4,743,669 | 5/1988 | Young | 527/200 |
| 4,755,265 | 7/1988 | Young | 204/45.1 |
| 4,801,511 | 1/1989 | Young | 429/198 |
| 4,818,269 | 4/1989 | Young | 71/83 |
| 4,831,056 | 5/1989 | Young | 514/588 |

(List continued on next page.)

FOREIGN PATENT DOCUMENTS 0243522  11/1987  European Pat. Off. .

OTHER PUBLICATIONS

Buhler et al., "Effect of Water Quality, Carrier Volume and Acid on Glyphosate Phytotoxicity", Weed Science, 1983, 31:163–169.

D. F. duToit, Verslag Akad. Wetenschappen, 22 5/3–4 (abstracted in Chemmical Abstracts, 8, 2346, (1914)).

L. H. Dalman, "Ternary Systems of Urea and Acids. I. (List continued on next page.)

Primary Examiner—Glennon H. Hollrah
Assistant Examiner—Brian G. Bembenick
Attorney, Agent, or Firm—Yale S. Finkle; Gregory F. Wirzbicki; Michael H. Laird

[57] ABSTRACT

Herbicidal compositions are provided which contain combinations of glyphosate [N-(phosphonomethyl)glycine] and sulfuric acid, and/or combinations of glyphosate, sulfuric acid and a chalcogen-containing compound of the formula $R_1$—CX—$R_2$ wherein X is a chalcogen compound of the formula $R_1$—CX—$R_2$ wherein X is selected from oxygen and sulfur, $R_1$ and $R_2$ are independently selected from hydrogen, monovalent organic radicals, $NR_3R_4$ and $NR_5$, at least one of $R_1$ and $R_2$ being $NR_3R_4$ or $NR_5$, $R_3$ and $R_4$ are independently selected from hydrogen and monovalent organic radicals, and $R_5$ is a divalent organic radical. Such compositions contain reaction products of glyphosate and sulfuric acid, and/or of glyphosate, sulfuric acid and the chalcogen compound, and they may also contain excess glyphosate or sulfuric acid. They effect more rapid, more thorough, broader spectrum vegetation control, and are more stable chemically and less toxic than other glyphosate-containing herbicides.

18 Claims, No Drawings

U.S. PATENT DOCUMENTS

| | | | |
|---|---|---|---|
| 4,834,788 | 5/1989 | Young | 71/83 |
| 4,839,088 | 6/1989 | Young | 252/182.27 |
| 4,877,869 | 10/1989 | Young | 536/35 |
| 4,879,413 | 11/1989 | Buser et al. | 564/63 |
| 4,885,425 | 12/1989 | Young | 585/458 |
| 4,910,179 | 3/1990 | Young | 437/228 |
| 4,910,356 | 3/1990 | Young | 585/262 |
| 4,912,278 | 3/1990 | Young | 585/458 |
| 4,931,061 | 6/1990 | Young | 47/57.6 |
| 4,931,079 | 6/1990 | Young | 71/77 |
| 4,935,048 | 6/1990 | Young | 71/83 |
| 4,942,254 | 7/1990 | Young | 558/250 |
| 4,944,787 | 7/1990 | Young | 71/28 |
| 4,966,620 | 10/1990 | Young | 71/83 |
| 4,993,101 | 2/1991 | Young | 71/83 |
| 4,993,442 | 2/1991 | Young | 134/22.14 |
| 5,034,046 | 7/1991 | Young | 55/213 |
| 5,035,737 | 7/1991 | Young | 71/83 |
| 5,055,127 | 10/1991 | Young | 71/83 |
| 5,057,584 | 10/1991 | Young | 526/220 |
| 5,099,014 | 3/1992 | Young | 540/145 |
| 5,105,040 | 4/1992 | Young | 585/425 |
| 5,105,043 | 4/1992 | Young | 585/477 |

OTHER PUBLICATIONS

Urea, Nitric Acid and Water. II. Urea, Sulfuric Acid and Water. III, Urea, Oxalic Acid and Water"; JACS 56, 549–53 (1934).

Sulfur Institute Bulletin No. 10 (1964), "Adding Plant Nutrient Sulfur to Fertilizer".

E. Grossbard and D. Aktinson, "The Herbicide Glyphosate," Butterworths, Boston, 1985 (pp. 211–240).

Title 40, Code of Federal Regulations, Section 180.1019., Jul. 1, 1980.

Comparative Phytotoxicity of Glyphosate, SC–0224, SC–0545, and HOE–00661, Carlson and Burnside, Weed Science, 1984, 32, 841–844.

"Complexing Agents as Herbicide Additives," Turner and Loader, Weed Reserach, 1978, 18, 199–207.

"Effect of Water Quality, Carrier Volume and Acid on Glyphosate Phytotoxicity," Buehler and Burnside, Weed Science, 1983, 31:163–169.

"New Weed Management Practices In Orchards," Neil H. Phillips, Proceedings, 36th Annual California Weed Conference, Jan. 16–19, 1984, Sacramento, Calif.

GLYPHOSATE-SULFURIC ACID ADDUCT HERBICIDES AND USE

RELATED APPLICATIONS

This application is a continuation of application Ser. No. 887,288, HERBICIDE AND METHOD, filed May 22, 1992, now abandoned, which is a division of application Ser. No. 306,529, HERBICIDE AND METHOD, filed Feb. 3, 1989, now U.S. Pat. No. 5,116,401, which is a continuation of Ser. No. 890,076, HERBICIDE AND METHOD, filed Jul. 24, 1986, now abandoned, which is a continuation-in-part of applications, Ser. No. 771,260, HERBICIDAL COMPOSITIONS AND METHODS OF USE, filed Aug. 30, 1985, now abandoned; Ser. No. 673,358, METHODS FOR HYDROLYZING POLYSACCHARIDES AND COMPOSITIONS USEFUL THEREIN, filed Nov. 20, 1984, now U.S. Pat. No. 4,664,717; Ser. No. 442,296, SYSTEMIC HERBICIDAL COMPOSITIONS AND METHODS OF USE, filed Nov. 17, 1982, now abandoned; Ser. No. 444,667, METHODS FOR CONTROLLING VEGETATION, filed Nov. 26, 1982, now abandoned; and Ser. No. 453,496, ACID-CATALYZED REACTIONS AND COMPOSITIONS FOR USE THEREIN, filed Dec. 27, 1982, now U.S. Pat. No. 4,910,179 the latter of which is a continuation-in-part of applications Ser. No. 331,001, NON-CORROSIVE UREA-SULFURIC ACID COMPOSITIONS, filed Dec. 15, 1981, now U.S. Pat. No. 4,402,852; Ser. No. 330,904, NON-CORROSIVE UREA-SULFURIC ACID REACTION PRODUCTS, filed Dec. 15, 1981, now U.S. Pat. No. 4,404,116; Ser. No. 318,629, METHODS OF PRODUCING CONCENTRATED UREA-SULFURIC ACID REACTION PRODUCTS, filed Nov. 5, 1981, now U.S. Pat. No. 4,445,925; Ser. No. 318,368, TOPICAL FERTILIZATION METHODS AND COMPOSITIONS FOR USE THEREIN, filed Nov. 5, 1981, now U.S. Pat. No. 4,447,253; and Ser. No. 318,343, METHODS FOR PRODUCING UREA-SULFURIC ACID REACTION PRODUCTS, filed Nov. 5, 1981, now U.S. Pat. No. 4,397,675.

BACKGROUND OF THE INVENTION

1. Field of the Invention

This invention relates to the field of herbicidal compositions and particularly to systemic herbicidal compositions and methods for using such compositions to control vegetation.

2. Description of the Art

The unique herbicidal properties of glyphosate and several of its more soluble salts are renowned. As reported by Grossbard and Atkinson in "The Herbicide Glyphosate," Butterworths, Boston, 1985, and by J. E. Franz in U.S. Pat. No. 3,799,758, glyphosate is a broad spectrum, nonselective, post-emergent herbicide having high unit activity on a wide variety of both annual and perennial plants. It can be manufactured and applied as glyphosate per se or any one of a very broad variety of glyphosate derivatives and homologues which, according to Franz, include halogen; hydroxy; thio; ammonium; mono- and di-alkylamine; hydroxy-alkyl and alkenyl amine, hydrocarbyl, hydrocarbonoxyhydrocarbyl, halohydrocarbyl, and halo-hydrocarbonoxyhydrocarbyl esters and thioesters; aminohydrocarbyl; metallo-oxy including alkali and alkaline earth, copper, zinc, manganese and nickel-oxy; amminoxy; organic amminoxy; and/or strong acid salt derivatives and homologs. According to Franz, supra, the alkali, alkaline earth, ammonium and organic amine salts are preferred. The isopropylamine salt is marketed by Monsanto Chemical Company as Roundup ®.

According to Grossbard et al., supra, when glyphosate is contacted with plant foliage, it is translocated to the plant roots, rhyzomes, and apical meristemes giving it its systemic property and resulting in the total destruction of many resistant perennial weeds such as rhyzome sorghum halepense, Agropyron repens, Cirsium arvense, Cyprus spp., C. dactylon, and others. Glyphosate, per se, has relatively broad herbicidal utility since it is active on a variety of vegetation. It is systemic, non-persistent, and is readily metabolized by soil microorganisms to form plant nutrients, including phosphoric acid, ammonia, and carbon dioxide. Thus, glyphosate is environmentally attractive in comparison to many alternative herbicides. For these reasons, glyphosate-containing herbicides are marketed in over 100 countries and are used to control undesired vegetation in crop lands, plantations, orchards, industrial and recreational areas, and for home use.

As with all things in nature, however, there is always room for improvement. While glyphosate is a very active, broad spectrum, systemic, relatively environmentally safe herbicide, its solubility in water at 25° C. is only 1.2 weight percent and many of its homologues and salts are only slightly soluble or are essentially insoluble in water and organic solvents. For instance, Franz illustrated that the glyphosate-hydrochloric acid "salt" is essentially insoluble in either water or tetrahydrofuran. Glyphosate is expensive and, when applied at recommended dosages as the isopropylamine salt, it does not completely control all plant species and maximum control does not occur for 1 to 3 weeks depending on plant species, dosage, etc. Moreover, many of the organic amine salts preferred by Franz have negative environmental effects which are not exhibited by the parent compound itself. For instance, the isopropylamine salt is toxic to fish and is not approved, at least not in the United States, for use on aquatic vegetation. The active portion of the molecule in the deliverable (water soluble) compounds—the glyphosate segment—is relatively chemically unstable even in weakly basic environments. Thus, glyphosate is hydrolyzed in weak base which may account for its failure to control vegetation in some instances. Mineral dust which accumulates on vegetation is generally alkaline, and hydrolysis which can occur in that environment (presumably at the amide link in the compound) deactivates glyphosate as a herbicide.

Several investigators have found that the herbicidal activity of glyphosate and its compounds can be increased in certain respects by formulation with other compounds. For instance, Grossbard and Atkinson, supra, report at page 226, that, under suitable conditions, ammonium salts, such as ammonium sulfate, can increase the phytotoxicity of a variety of water-soluble leaf-applied herbicides, including certain water-soluble glyphosate derivatives. According to Grossbard et al., these effects are evident particularly when ammonium salts such as ammonium sulfate are combined with the appropriate surfactant (ibid., page 228). The effects of several other compounds have also been investigated. For instance, Grossbard et al., report, at page 229, that ammonium salts other than ammonium sulfate have shown improved herbicidal effects in isolated studies and that those effects are less than have been observed in other instances with ammonium sulfate. They also report that, in one test on C. rotundas, slight improvement in glyphosate activity was observed upon addition of urea to the formulation. Other investigators have studied the relative effects of hydrophilic and lipophilic surfactants in the presence or absence of other components such as ammonium salts (Grossbard et al., ibid., page 228). Polybasic acids such as orthophosphoric and oxalic acids reportedly have shown improvement for the control for Agropyron repens when used in combination with certain soluble glyphosate derivatives (Grossbard et al., supra, page 230). While the precise mode of action of the previously tested ammonium salts, surfactants, polybasic acids, and other additives is not known with certainty, it has been suggested that certain ammonium salts modify plant membrane permeability but do not appear to directly influence translocation, while the polybasic acids may improve activity of the isopropylamine salt by sequestering and/or immobilizing metals such as calcium (ibid, page 230). However, the herbicidal effectiveness, per se, of glyphosate compounds and compositions, according to Franz, is not affected by the type of salt, i.e., the glyphosate counter-ion. Thus, in the chapter dealing with the discovery, development, and chemistry of glyphosate published by Grossbard et al., supra, Franz states that "[a]fter penetration into leaf tissue, therefore, glyphosate exists in the apoplast primarily in its monoanionic form and is translocated via the phloem as the dianion. The similar herbicidal effectiveness of glyphosate acid and many of its soluble salts . . . indicates that the counter-ion may influence formulation solubility but not overall biological activity." (Grossbard et al., supra, p. 9)

SUMMARY OF THE INVENTION

Briefly, the invention provides novel liquid, water-soluble, herbicidal combinations of glyphosate, or its derivatives, and sulfuric acid and/or combinations of glyphosate, sulfuric acid and chalcogen compounds of the formula $R_1$—CX—$R_2$ where X is oxygen or sulfur, $R_1$ and $R_2$ are independently selected from hydrogen, monovalent organic radicals, $NR_3R_4$ and $NR_5$ wherein $R_3$ and $R_4$ are independently selected from hydrogen and monovalent organic radicals and $R_5$ is a divalent organic radical, provided that at least one of $R_1$ and $R_2$ is $NR_3R_4$ or $NR_5$. These combinations contain (or form upon evaporation of solvent) reaction products of glyphosate, or its derivatives, and sulfuric acid and/or of glyphosate, sulfuric acid and the defined chalcogen compounds. The invention also provides novel methods for controlling vegetation with such compositions.

These compositions possess many advantages in comparison to glyphosate and its homologs and derivatives, including the metal and amine salts preferred by Franz, supra, and the commercially available, water soluble organic amine salts (e.g., Roundup). The sulfuric acid-containing combinations are much more soluble than glyphosate, and they are substantially more chemically stable, less toxic, less costly to manufacture, and more active on a wider variety of vegetation than the amine salts such as the isopropylamine salt. The glyphosate-sulfuric acid and glyphosate-sulfuric acid-chalcogen compound compositions may be either solids or liquids, and concentrated liquid systems can be produced which contain only glyphosate and sulfuric acid and which are solvent-free, completely stable at room temperature, and miscible with water or other polar solvents in all proportions. Thus, they eliminate the need for toxic, expensive organic amine derivatives, such as the isopropylamine salt, which can be toxic to the environment and to animals such as fish. Yet they provide concentrated, water-soluble, chemically stable, fast-acting, broad spectrum, non-caustic, herbicidal formulations which easily can be manufactured, shipped, stored and applied. Thus, these compositions and methods reduce the expense and the environmental and health hazards involved in plant control by reducing the cost and toxicity of the herbicidal agent and the quantity of material which must be applied. It also has been found that glyphosate attenuates several properties of sulfuric acid, including its corrosivity.

The novel compositions are faster acting and broader spectrum herbicides, and they provide rapid, thorough control of species not adequately controlled by the organoamine-glyphosate formulations. In effect, they broaden the range of species on which the glyphosate component is active. In particular, the compositions of this invention are more active for the control of broad leaf plants than are other glyphosate-containing formulations. They are also more chemically stable than other compositions containing glyphosate since they minimize the activity loss which otherwise results from hydrolysis of the glyphosate unit under alkaline conditions which may exist on dusty plant foliage, in application equipment, and in water used for dilution.

The chemical stability and apparent potentiation of glyphosate in the novel compositions may be due, in part, to direct potentiation of glyphosate activity by the acid and urea components and to the resistance to base hydrolysis which may be imparted by the sulfuric acid component. While sulfuric acid apparently potentiates glyphosate's herbicidal activity and improves its chemical stability and solubility, the glyphosate component, in effect, tames the acid by attenuating its corrosivity and reactivity to equipment, personnel, and clothing. For instance, while the 1/1 glyphosate/$H_2SO_4$ molar ratio reaction product contains 36 weight percent sulfuric acid, it does not immediately burn skin or char clothing as would aqueous solutions containing an equivalent amount of free sulfuric acid.

Due to these and other advantageous characteristics, the glyphosate-sulfuric acid-containing compositions of this invention reduce the expense involved in vegetation control; they are easier to handle, store, ship, and apply. They are less toxic to the environment, and impart less residue in crops due to their higher specific activity.

DETAILED DESCRIPTION OF THE INVENTION

The herbicidal compositions of this invention involve combinations of sulfuric acid and glyphosate [N-(phosphono-methyl)glycine] and of sulfuric acid, glyphosate, and chalcogen compounds of the formula $R_1$—CX—$R_2$ where X is oxygen or sulfur, $R_1$ and $R_2$ are independently selected from hydrogen, monovalent organic radicals, $NR_3R_4$ and $NR_5$ wherein $R_3$ and $R_4$ are independently selected from hydrogen and monovalent organic radicals and $R_5$ is a divalent organic radical, provided that at least one of $R_1$ and $R_2$ is $NR_3R_4$ or $NR_5$. These combinations contain (or form upon evaporation of solvent) reaction products of glyphosate, or its derivatives, and sulfuric acid and/or of glyphosate, sulfuric acid and the described chalcogen compounds.

The methods involve the control of vegetation with such compositions.

It has been found that sulfuric acid is capable of reversibly reacting with glyphosate and with combinations of glyphosate and the described chalcogen compounds under certain reaction conditions, and that glyphosate reaction products of sulfuric acid can be formed. Under appropriate conditions, as described herein, a glyphosate-chalcogen compound reaction product with sulfuric acid, which contains one mole of each of the three constituents, can also be formed. Application of any one or a combination of these constituents to plant foliage rapidly and effectively controls the treated plant.

Surprisingly, concentrated sulfuric acid, a strong Lowry-Bronsted acid and very strong dehydrating agent, does not dehydrate the glyphosate component as it does sugars and many other organic compounds. Nor does it react with glyphosate to form a crystalline, water-insoluble salt as reported by Franz, for concentrated hydrochloric acid. The 1/1 glyphosate/sulfuric acid reaction product is a water-soluble, chemically and physically stable, non-corrosive, non-toxic liquid at ambient conditions. The 1/1/1 glyphosate/chalcogen compound/$H_2SO_4$ molar product is soluble in water at ambient conditions, and is also a chemically and physically stable, non-toxic, non-corrosive liquid. Sulfuric acid-glyphosate reaction products which contain 2 moles of sulfuric acid per mole of glyphosate can also be formed. Excess sulfuric acid may also be present, although such combinations are presently less preferred due to their higher corrosivity. In contrast, combinations of glyphosate and hydrochloric acid form water-insoluble, corrosive, toxic, chemically unstable mixtures which gradually evolve hydrogen chloride, ultimately leaving only glyphosate.

The sulfuric acid reaction products with glyphosate or with glyphosate and the chalcogen compounds are adducts of sulfuric acid and glyphosate or of sulfuric acid, glyphosate, and the chalcogen compound.

The optional chalcogen-containing compounds which also can be employed in these formulations have the empirical formula:

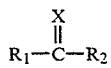  (4)

wherein X is oxygen or sulfur and $R_1$ and $R_2$ are independently selected from hydrogen, monovalent organic radicals, $NR_3R_4$ and $NR_5$, with at least one of $R_1$ and $R_2$ being $NR_3R_4$ or $NR_5$. $R_3$ and $R_4$ are independently selected from hydrogen and monovalent organic radicals, and $R_5$ is a divalent organic radical. When $R_1$, $R_2$, $R_3$, and/or $R_4$ are monovalent organic radicals, such radicals can include, for instance, alkyl, aryl, alkenyl, alkenylaryl, aralkyl, aralkenyl, cycloalkyl, cycloalkenyl, or alkynyl, which can be substituted or unsubstituted with pendant functional groups such as hydroxyl, carboxyl, oxide, thio, thiol, or others, and they can contain heteroatoms such as oxygen, sulfur, nitrogen, or others. $R_5$ can be any divalent organic radical such as alkdyl, ardyl, alkendyl, alkyndyl, aralkdyl, aralkendyl, etc., which may contain pendant atoms or substituents and/or heteroatoms as described for $R_3$ and $R_4$. Preferably, $R_3$ and $R_4$ are hydrogen or hydrocarbyl radicals which, in combination, contain about 10 carbon atoms or less, and X is preferably oxygen. Such substituents are presently preferred due to their relatively higher chemical stability. Particularly preferred chalcogen-containing compounds include urea, thiourea, formamide, and combinations of these.

Essentially any proportions of glyphosate and sulfuric acid can be employed, it being essential only that a sufficient quantity of each constituent is present to obtain a herbicidally effective amount of one or more of the glyphosate-sulfuric acid reaction products. It has been found that the glyphosate-sulfuric acid and glyphosate-chalcogen compound-sulfuric acid reaction products are more soluble and more herbicidally active than glyphosate alone and that such adducts control a broader range of vegetation than does glyphosate or the organoamine glyphosate salts such as the isopropylamine salt. Accordingly, the compositions of this invention can contain only minor amounts of one or more of the described reaction products in the presence or absence of excess glyphosate or sulfuric acid. As a rule, however, a substantial proportion of the glyphosate and sulfuric acid is present as one or more of such reaction products. Accordingly, the glyphosate/$H_2SO_4$ molar ratio will usually be at least about 0.1, generally at least about 0.5. Compositions having glyphosate/$H_2SO_4$ molar ratios of 0.5 contain (or form upon evaporation of solvent from dilute solutions) 50 percent of the sulfuric acid as the mono-glyphosate-sulfuric acid reaction product. The glyphosate/$H_2SO_4$ molar ratio is generally below about 10, usually below about 5 and preferably about 2 or less. Most compositions will have glyphosate/$H_2SO_4$ molar ratios within the range of about 0.1 to about 10, preferably about 0.1 to about 2. The mono-glyphosate-sulfuric acid composition, e.g., the reaction product of one mole of each reactant at 70° F., contains 63.3 weight percent glyphosate and 36.7 weight percent sulfuric acid which correspond to a glyphosate/$H_2SO_4$ molar ratio of one. Reaction products which are presently preferred, particularly for manufacture and/or use as concentrates containing, for example, 5 weight percent or more of the combination of glyphosate and sulfuric acid, have glyphosate/$H_2SO_4$ molar ratios of about 1/2 to about 1/1. Within this molar ratio range, stable, noncorrosive liquid compositions and concentrated solutions can be obtained. When the glyphosate/$H_2SO_4$ molar ratio of such compositions is increased much above 1/1 in concentrated liquids or solutions, a solid phase tends to precipitate. When the molar ratio is reduced much below 1/3 (i.e., 3 moles of sulfuric acid per mole of glyphosate), the combinations can become corrosive indicating that the oxidizing and dehydrating activities of sulfuric acid are not completely attenuated by glyphosate.

The novel compositions also include combinations which contain one of the described chalcogen compounds in addition to glyphosate and sulfuric acid. The presence of the chalcogen compound results in the formation of the glyphosate-chalcogen compound-sulfuric acid reaction product which contains at least one mole of each of the three constituents. Very minor amounts of the chalcogen compound relative to glyphosate and sulfuric acid can be employed. However, when the chalcogen compound is employed, the chalcogen compound/$H_2SO_4$ molar ratio will usually be at least about 0.1, generally at least about 0.5, preferably about 0.5 to 2, and most preferably about 1.

The presence of the glyphosate-sulfuric acid reaction products and of the glyphosate-chalcogen compound-sulfuric acid reaction products has been established by several observations. For instance, glyphosate, which is soluble in water only to the extent of 1.2 weight percent at 25° C., dissolves in concentrated (100%) sulfuric acid to the extent of 63.3 weight percent. Secondly, dissolution of glyphosate in concentrated sulfuric acid produces a significant exotherm indicating that a reaction between glyphosate and sulfuric acid occurs. Furthermore, several of the characteristic chemical activities of sulfuric acid are largely attenuated or are not even evident when the acid is combined with glyphosate. The reaction products do not char cellulose or other materials which are normally attacked by concentrated sulfuric acid. Nevertheless, the sulfuric acid still exists as the acid and has not been neutralized, e.g., by conversion to a Bronsted salt, as evidenced by titration with standard base. The same is true of the chalcogen compound-containing compositions. Addition of one of the described chalcogen compounds to compositions containing glyphosate and sulfuric acid produces an exotherm characteristic of the reaction of urea with sulfuric acid which occurs in the formation of urea-sulfuric acid adducts as discussed in my U.S. Pat. No. 4,445,925, Methods of Producing Concentrated Urea-Sulfuric Acid Reaction Products, the disclosure of which is incorporated herein in its entirety.

Several of the novel glyphosate-sulfuric acid reaction products can be manufactured as solids, while all of the described reaction products can be manufactured and employed as pure liquids or solutions. For instance, the mono-glyphosate product (glyphosate/$H_2SO_4$ mole ratio of 1/1) is liquid under ambient conditions in the absence of any solvent, and is miscible in all proportions with water and other polar solvents.

The novel reaction products are usually applied to vegetation in liquid form, and such liquids contain herbicidally effective amounts of the glyphosate-sulfuric acid reaction products. While these reaction products exhibit herbicidal activity at very minor concentrations and dosage rates, the glyphosate is usually present in the composition at a concentration of at least about 0.05 weight percent and preferably at least about 0.1 weight percent. Higher concentrations are usually preferred for manufacture, shipment, and storage. In such compositions, glyphosate concentration will be at least about 10 weight percent, generally, at least about 20 weight percent, preferably at least 30 weight percent, and can even exceed 50 weight percent. As disclosed herein, glyphosate concentrations as high as 63.3 weight percent can be achieved in the liquid compositions.

The novel liquid and solid compositions can contain one or more other materials which do not negate the herbicidal activity of the glyphosate-sulfuric acid reaction product. Such additional materials typically include surfactants which facilitate foliage wetting and corrosion inhibitors such as those discussed in my U.S. Pat. Nos. 4,402,852, NON-CORROSIVE UREA-SULFURIC ACID COMPOSITIONS, and 4,404,116, NON-CORROSIVE UREA-SULFURIC ACID REACTION PRODUCTS, the disclosures of which are incorporated herein by reference in their entireties.

Glyphosate can be prepared by the reaction of glycine with chloromethylphosphonic acid as described by J. E. Franz in U.S. Pat. No. 3,799,758, the disclosure of which is incorporated herein by reference in its entirety. Alternative schemes for the manufacture of glyphosate are discussed and/or referenced by Grossbard et al., supra.

The active glyphosate-sulfuric acid reaction products can be prepared by adding sulfuric acid to glyphosate or adding glyphpsate to either dilute or concentrated sulfuric acid. The resultant reactions of glyphosate and sufluric acid are exothermic. While glyphosate is thermally stable at temperatures of up to about 200° C., it is preferable to maintain much lower temperatures in the presence of strong acids, such as sulfuric acid. Thus, it is presently preferred to assure that reaction temperature is maintained at about 70° C. or less in concentrated systems, e.g., systems in which the glyphosate and sulfuric acid, in combination, constitute at least about 20 weight percent of the combination, and particularly when they constitute more than 40 percent of the composition.

Glyphosate-sulfuric acid compositions having glyphosate/$H_2SO_4$ molar ratios of about 1 can be prepared in liquid form at room temperature in -the absence of any solvent. Compositions which contain substantial excesses of glyphosate, however, will precipitate.

The novel glyphosate-chalcogen compound-sulfuric acid herbicides can be prepared by adding the chalcogen compound to preformed glyphosate-sulfuric acid reaction products, by the simultaneous or sequential addition of the chalcogen compound and glyphosate to sulfuric acid, the addition of sulfuric acid to solutions of the chalcogen compound and glyphosate, or by the addition of glyphosate to pre-formed chalcogen compound-sulfuric acid adducts. When pre-formed glyphosate-sulfuric acid reaction products or chalcogen compound-sulfuric acid reaction products are employed in such preparations, it is presently preferred, although not essential, that the pre-formed material have a glyphosate/$H_2SO_4$ or chalcogen compound/$H_2SO_4$ molar ratio below 2. This proviso will assure the availability of reactive sites on the sulfuric acid for reaction with the third component, e.g., either glyphosate or the chalcogen compound. Methods suitable for preparing urea-sulfuric acid adducts are discussed in my U.S. Pat. No. 4,445,925, supra, and adducts of the other chalcogen compounds described herein can be prepared by those methods.

Essentially all varieties of vegetation can be controlled by applying to the foliage a herbicidally effective amount of the glyphosate-sulfuric acid and/or glyphosate-chalcogen compound-sulfuric acid combinations. While very minor dosage rates of the novel combinations deter plant growth, adequate control usually involves the application of sufficient herbicide to either eliminate undesired vegetation or deter its growth. Dosage rates required to accomplish these effects, of course, vary depending on plant type (due to variations in specific plant resistance) and plant size and maturity. More mature plants are generally more resistant to herbicides and require higher dosage rates for a comparable level of control. Useful dosage rates can best be expressed in relation to glyphosate dosage rates and will generally correspond to at least about 0.1 pints glyphosate per acre, preferably at least about 0.2 pints per acre. Dosage rates corresponding to glyphosate dosages of about 0.2 to about 20 pints per acre are generally adequate to control most weeds and brush prevalent in field crop areas. The described glyphosate dosage rates correspond broadly to at least about 1, preferably at least about 2, and usually about 2 to about 200 pounds per acre of the combination of glyphosate and sulfuric acid or glyphosate-chalcogen compound-sulfuric acid (on a solvent-free basis).

The described herbicides can be employed to effectively control both dry-land and aquatic vegetation including all varieties of grasses, broad leafs, and succulents ranging from crabgrass to all varieties of forest trees, including broad leafs and conifers. Illustrative of undesired vegetation typically controlled for dry-land agricultural purposes are: black mustard (brassica nigra), curly dock (rumex crispus), common groundsel (senecio vulgaris), pineapple weed (matricaria matricarioides), swamp smartweed (kelp) (polygonum coccineum), prickly lettus (lactuca scarjoia), lance-leaved groundcherry (physalis lanceifolia), annual sow-thistle (sonchus oleraceus), london rocket (sisymbrium irio), common fiddleneck (amsinckia intermedia), hairy nightshade (solanum sarrachoides), shepherd's purse (capsella bursa-pastoris), sunflower (helianthus annus), common knotweed (polygonum aviculare), green amaranth (amaranthus hybridus), mare's tail (conyza canadensis), henbit (lamium amplexicaule), cocklebur (xanthium strumarium), cheeseweed (malva parviflora), lambs-quarters (chenopodium album), puncture vine (tribulus terrestris), common putslane (portulaca oleracea), prostrate spurge (euphorbia supina), telegraph plant (heterotheca grandiflora), carpetweed (mollugo verticillata), yellow starthistle (centaurea solstitialis), milk thistle (silybum mariahum), mayweed (anthemis cotula), burning nettle (urtica urens), fathen (atriplex patula), chickweed (stellaria media), scarlet pimpernel (anagallis arvensis), redroot pigweed (amaranthus retroflexus), minners lettuce (montia perfoliata), turkey mullein (eremocarpus setigerus), nettle-leaf goosefoot (chenopodium murale), prostrate pigweed (amaranthus blitoides), silverleaf nightshade (solanum elaeagnifolium), hoary cress (cardaria draba), largeseed dodder (cuscuta indecora), california burclover (medicago polymorpha), horse purslane (trianthema portulacastrum), field bindweed (Iconvolvulus arvensis), Russian knapweed (centaurea repens), flax-leaved fleabane (conyza bonariensis), wild radish (raphanus sativus), tumble pigweed (amaranthus albus), stephanomeria (stephanomeria exigua), wild turnip (brassica campestris), buffalo goard (cucurbita foetidissima), common mullein (verbascum thapsus), dandelion (taraxacum officinale), spanish thistle (xanthium spinosum), chicory (cichorium intybus), sweed anise (foeniculum vulgate), annual yellow sweetclover (melilotus indica), poison hemlock (conium maculatum), broadleaf filaree (erodium botrys), white stem filaree (erodium moschatum), redstem filaree (erodium cicutarium), ivyleaf morning-glory (ipomea hederacea), shortpod mustard (brassica geniculata), buckhorn plantain (plantago lacenolata), sticky chickweed (cerastium viscosum), himalaya blackberry (rubus procerus), purslane speedwell (veronica peregrina), mexicantea (chenopodium ambrosioides), spanish clover (lotus purshianus), australian brassbuttons (cotula australis), goldenrod (solidago californica), citron (citrullus lanatus), hedge mustard (sisymbrium orientale), black nighshade (solanum nodiflorum), chinese thornapple (datura ferox), bristly oxtongue (picris echioides), bull thistle (cirsium vulgare), spiny sowthistle (sonchus asper), tasmanjan goosefoot (chenopodium pumilio), goosefoot (chenopodium botrys), wright groundcherry (physalis acutifolia), tomatillo groundcherry (physalis philadelphica), pretty spurge (euphorbia peplus), bitter apple (cucumis myriocarpus), indian tobacco (nicotiana bigelovii), common morning-glory. (ipomoea purpurea), waterplantain (alisma triviale), smartweed (polygonum lapathifolium), mature sowthistle (sonchus asper), yellow nutsedge (cyperus esculentus), purple nutsedge (cyperus rotundus), lupine (lupinus formosus), and grasses of the family Gramineae such as annual rye grass, .blue grass, water grass, barnyard grass, bermuda grass, fescue, mat grass, Johnson grass, and the like.

The invention is further described by the following examples which are illustrative of specific modes of practicing the invention and are not intended as limiting the scope of the invention defined by the appended claims.

EXAMPLE 1

Four replicate test plots of 0.1 acre each comprising mature populations of Pigweed, Sowthistle, Barnyard grass, jungle grass and Cheeseweed were treated with the glyphosate-isopropylamine salt (as Roundup®) applied at a rate of two quarts per acre in a total spray volume of 50 gallons per acre. All weed populations were mature and had an average plant height of approximately one foot. Three days after application, the extent of damage to all plants of each species in each replicate test plot was evaluated and rated on a scale of 1 to 10, 1 indicating no damage whatever and 10 indicating complete necrosis. These results are reported in column A under each respective weed species in Table 1. Evaluation of weed control was repeated 5 days after application using the same indexing system. These results are reported under column B for each weed species in Table 1.

EXAMPLE 2

The operation described in Example 1 was repeated on four replicate test plots in the same weed population with the exception that the glyphosate-isopropylamine salt was applied at a rate of one quart per acre. All other conditions remained the same. The results of this test are reported for each weed species in Table 1.

EXAMPLE 3

The operation described in Example 1 was repeated on four additional replicate test plots in the same weed population with the exception that the glyphosate-isopropylamine salt was applied at a rate corresponding to 0.25 quart per acre (as Roundup). All other conditions remained the same. The results for each weed species are reported in Table 1.

EXAMPLE 4

The operation described in Example 1 was repeated on four additional replicate test plots of the same weed population with the exception that the plants in these test plots were treated by foliar application of a glyphosate-sulfuric acid composition having a glyphosate/$H_2SO_4$ molar ratio of one. This composition was applied at a rate, based on equivalent glyphosate content, corresponding to two quarts per acre of the glyphosate-isopropylamine salt. In other words, the quantity of glyphosate applied in this application was equivalent to the quantity of glyphosate existing in two quarts of the glyphosate-isopropylamine salt (expressed as Roundup). This composition was diluted to a total spray volume of 50 gallons per acre prior to application. Damage to each weed species was evaluated as in Example 1, and those results are reported in Table 1.

EXAMPLE 5

The operation described in Example 4 was repeated with the exception that the glyphosate-sulfuric acid composition was applied to four additional replicate test plots in the same weed population at a dosage rate corresponding to one quart per acre equivalent glyphosate-isopropylamine salt (based on glyphosate equivalent). Evaluation of weed damage was repeated as in Example 1, and the results are reported in Table 1.

EXAMPLE 6

The operation described in Example 4 was repeated on four additional test plots in the same weed population with the exception that the glyphosate-sulfuric acid composition was applied at a rate corresponding to 0.25 quart per acre equivalent glyphosate-isopropyl amine salt. All other conditions were the same as in Example 4, and evaluation of weed damage was repeated as in Example 1. Results of these evaluations are reported in Table 1.

TABLE 1

|  | Rate[b] | Degree of Control[c] | | | | | | | | |
|---|---|---|---|---|---|---|---|---|---|---|
|  |  | Pigweed | | Sowthistle | | Bernard Grass | | Jungle Grass | | Cheeseweed |
|  | qt./@ | A | B | A | B | A | B | A | B | A | B |
| 1. Glyphosate- | 2 | 7 | 10 | 4 | 7 | 9 | 10 | 8 | 10 | 2 | 5 |
| isopropyl- | 1 | 7 | 10 | 4 | 6 | 9 | 10 | 8 | 10 | 2 | 5 |
| amine salt[a] | 0.25 | 6 | 9 | 3 | 6 | 9 | 10 | 8 | 10 | 2 | 4 |
| 2. Glyphosate- | 2 | 9 | 10 | 8 | 10 | 9 | 10 | 9 | 10 | 8 | 10 |
| H2SO4 reaction | 1 | 9 | 10 | 8 | 9 | 9 | 10 | 9 | 10 | 7 | 10 |
| product | 0.25 | 6 | 6 | 3 | 5 | 7 | 8 | 7 | 8 | 5 | 5 |

[a] As Roundup ®.
[b] Rates for glyphosate-H2SO4 reaction product expressed as molar equivalent quantity of isopropylamine salt.
[c] 1 = no control. 10 = complete control. Column A evaluated 3 days after application; column B evaluated 5 days after application.

Comparison of the results of Examples 1 through 6 demonstrates that the glyphosate-sulfuric acid compositions of this invention achieved earlier control of all weed species then the glyphosate-isopropylamine salt (results of column A) with the exception of Barnyard Grass. All compositions demonstrated good control of Barnyard Grass at the first date of evaluation. These results further demonstrate that the glyphosate-sulfuric acid compositions provided better long term control of several weed species including Sowthistle and Cheeseweed and effected essentially equivalent control of Pigweed, Barnyard Grass and Jungle Grass.

EXAMPLE 7

Round-up ® and the 1/2 glyphosate/$H_2SO_4$ molar ratio reaction product were applied to separate test plots of mature winter weeds comprising mixed species of susceptible grasses and broadleafs as well as some broadleaf varieties generally more tolerant to Round-up. Round-up applications were made at rates of 8, 16, and 24 ounces per acre of a solution purchased as Round-up and formulated to contain three pounds equivalent glyphosate per gallon. Each dosage rate was applied at three different spray volumes—10, 30, and 50 gallons per acre, and each test was replicated four times for a total of 36 trials. Each test plot was visually inspected 7, 15, and 25 days after spraying, and the results are reported in Table 2 following Example 8, infra.

Predominant grasses included ripgut brome (bromus rigidus), and wild barley (hordeum leporinum). Predominant broadleaf weeds were wild radish (raphanus sativus), mares tail (conyza canadensis), red stem filaree (erodium cicutarium), almond seedlings (prunus sp.), groundsel (senecio vulgaris), annual sowthistle (sonchos oleiaceus), chickweed (stellaria media), and fiddleneck (amsinckia intermedia). Minor broadleaf weeds were red maids (calandrinia ciliata) and wire weed (polygonum aviculare). The only significant perennial weed was bermuda grass (cynodon dactylon).

EXAMPLE 8

The field trial described in Example 7 was repeated with the exception that the herbicide applied was a glyphosate/sulfuric acid reaction product containing 2 moles of sulfuric acid per mole of glyphosate and sufficient water to obtain a composition containing three pounds equivalent glyphosate per gallon. As in Example 7, this material was applied at dosage rates of 8, 16, and 24 fluid ounces per acre, and each dosage rate was applied at spray volumes of 10, 30 and 50 gallons per acre. There were four replicates of each trial. Weed vigor ratings for the thirteen weed species grouped as grasses and broadleafs were evaluated 7, 15, and 25 days after spraying and these results are reported in Table 2.

TABLE 2

|  |  |  | Weed Vigor Rating(a) | | | | | |
|---|---|---|---|---|---|---|---|---|
|  |  |  | Grasses | | | Broadleafs | | |
| Herbicide | oz./@ | gal/@ | 7 days | 15 days | 25 days | 7 days | 15 days | 25 days |
| Round-up ® | 8 | 10 | 0 | 6 | 8 | 0 | 4 | 4 |
| S.A.G.(b) | 8 | 10 | 0 | 6 | 7 | 0 | 5 | 6 |
| Round-up | 16 | 10 | 0 | 7 | 8 | 0 | 5 | 5 |
| S.A.G. | 16 | 10 | 0 | 8 | 9 | 0 | 7 | 8 |
| Round-up | 24 | 10 | 3 | 8 | 9 | 2 | 7 | 8 |
| S.A.G. | 24 | 10 | 2 | 9 | 10 | 0 | 9 | 10 |
| Round-up | 8 | 30 | 0 | 5 | 6 | 0 | 3 | 3 |
| S.A.G.(b) | 8 | 30 | 0 | 7 | 8 | 0 | 5 | 7 |
| Round-up | 16 | 30 | 0 | 6 | 7 | 0 | 4 | 4 |
| S.A.G. | 16 | 30 | 0 | 8 | 8 | 0 | 6 | 7 |
| Round-up | 24 | 30 | 4 | 8 | 8 | 3 | 7 | 7 |
| S.A.G. | 24 | 30 | 3 | 9 | 10 | 2 | 7 | 9 |
| Round-up | 8 | 50 | 0 | 3 | 5 | 0 | 2 | 3 |
| S.A.G.(b) | 8 | 50 | 0 | 6 | 9 | 0 | 5 | 7 |
| Round-up | 16 | 50 | 0 | 6 | 7 | 0 | 4 | 4 |
| S.A.G. | 16 | 50 | 0 | 8 | 9 | 0 | 7 | 8 |
| Round-up | 24 | 50 | 4 | 6 | 8 | 3 | 5 | 6 |
| S.A.G. | 24 | 50 | 2 | 9 | 10 | 0 | 8 | 10 |

(a) 0 = healthy plant; 10 = dead plant.
(b) S.A.G. = sulfuric acid/glyphosate reaction product, 2/1 molar.

The results reported in Table 2 demonstrate that, with only two exceptions in which the herbicides were equivalent, the sulfuric acid-glyphosate reaction product was consistently more effective than the glyphosate isopropylamine salt (Round-Up ®) at 15 and 25 days after application on both grasses and broadleafs at all dosage rates and spray volumes. The sulfuric acidglypohosate reaction product exhibited equivalent herbicidal activity on both grasses and broadleafs at all dosage and spray volumes; the isopropylamine salt did not. The salt exhibited significantly less herbicidal activity on broadleafs than it did on grasses. The sulfuric acid-glyphosate reaction product also exhibited equivalent activity at all dilutions (spray volumes), while the isopropylamine salt did not. For instance, the activity of the sulfuric acid-glyphosate reaction product applied at 50 gallons per acre spray volume was equivalent, and possibly superior to, its activity at the lower spray volumes of 10 and 30 gallons per acre. In contrast, the activity of the isopropylamine salt diminished markedly with dilution. Thus, the activity of the salt at 50 gallons per acre spray volume was consistently less than at 10 and 30 gallons per acre for both grasses and broadleaf weeds.

While particular embodiments of the invention have been described, it will be understood, of course, that the invention is not limited thereto since many obvious modifications can be made, and it is intended to include within this invention any such modifications as will fall within the scope of the appended claims. For instance, sulfuric acid reaction products with herbicidally active derivatives and homologs of glyphosate have physical and herbicidal properties similar to those exhibited by the described sulfuric acid-glyphosate reaction products, and such reaction products are intended to be included within the scope of this invention.

I claim:

1. A compound consisting of glyphosate [N-(phosphonomethyl)glycine] and sulfuric acid in a 1:2 molar ratio of glyphosate-to-sulfuric acid.

2. A herbicidal composition comprising a herbicidally effective amount of the compound defined by claim 1.

3. A method for controlling vegetation which comprises contacting said vegetation with a herbicidally effective amount of the composition defined by claim 2.

4. A method for controlling vegetation which comprises mixing the compound defined by claim 1 with water and contacting said vegetation with a herbicidally effective amount of the resulting solution.

5. A composition as defined by claim 2 comprising at least about 10 weight percent glyphosate.

6. A composition as defined by claim 2 comprising at least about 20 weight percent combined glyphosate and sulfuric acid.

7. A composition as defined by claim 2 comprising at least about 5 weight percent combined glyphosate and sulfuric acid.

8. A composition as defined by claim 2 wherein said composition is an aqueous solution of said compound.

9. A method for controlling vegetation which comprises contacting said vegetation with a herbicidally effective amount of the composition defined by claim 8.

10. The compound formed by reacting 1 molecule of glyphosate [N-(phosphonomethyl)glycine] with 2 molecules of sulfuric acid.

11. A method for controlling vegetation which comprises mixing the composition defined by claim 5 with water and contacting said vegetation with a herbicidally effective amount of the resulting solution.

12. A method for controlling vegetation which comprises mixing the composition defined by claim 7 with water and contacting said vegetation with a herbicidally effective amount of the resulting solution.

13. A method for controlling vegetation which comprises diluting the composition of claim 6 with water and contacting said vegetation with a herbicidally effective amount of the resulting aqueous solution.

14. A process comprising reacting glyphosate [N-(phosphonomethyl)glycine] and sulfuric acid present in substantially a 2:1 molar ratio of sulfuric acid-to-glyphosate.

15. A process as defined by claim 14 wherein said glyphosate and said sulfuric acid are reacted at a temperature below about 70° C.

16. A process as defined by claim 14 wherein said reactants are reacted essentially to completion, 17. A composition as defined by claim 2 wherein the glyphosate-to-sulfuric acid molar ratio is within the range of 0.1 to 2.

18. A composition as defined by claim 2 wherein the glyphosate-to-sulfuric acid molar ratio is within the range of 0.5 to 1.0.

* * * * *

UNITED STATES PATENT AND TRADEMARK OFFICE
CERTIFICATE OF CORRECTION

PATENT NO. : 5,411,944
DATED : May 2, 1995
INVENTOR(S) : Donald C. Young

It is certified that error appears in the above-indentified patent and that said Letters Patent is hereby corrected as shown below:

Title page, Item [60], column 1, line 13 under "Related U.S. Application Data", after "Dec. 15," delete "1991" and insert -- 1981 --.

Column 6, line 34, after "reactant" and before "at" insert -- is a stable liquid --; line 34, after "70°F." insert -- and it --.

Signed and Sealed this

Tenth Day of October, 1995

Attest:

BRUCE LEHMAN

Attesting Officer

Commissioner of Patents and Trademarks